US005710030A

United States Patent [19]

Anderson

[11] Patent Number: 5,710,030
[45] Date of Patent: Jan. 20, 1998

[54] PROCESS FOR PREPARING FUELS, FUEL SUBSTITUTES, AND FUEL SUPPLEMENTS FROM RENEWABLE RESOURCES

[75] Inventor: Kevin W. Anderson, Hamilton, Ohio

[73] Assignee: Henkel Corporation, Plymouth Meeting, Pa.

[21] Appl. No.: 527,701

[22] Filed: Sep. 13, 1995

[51] Int. Cl.$^6$ .................................. C12P 7/64; C12P 7/62
[52] U.S. Cl. ............................................. 435/134; 435/135
[58] Field of Search .................................... 435/134, 135

[56] References Cited

U.S. PATENT DOCUMENTS

| 2,342,330 | 2/1944 | Christensen | 195/17 |
| 4,361,651 | 11/1982 | Keim | 435/161 |
| 4,409,329 | 10/1983 | Silver | 435/105 |
| 4,415,659 | 11/1983 | Ronkainen et al. | 435/161 |
| 4,425,433 | 1/1984 | Neves | 435/163 |
| 4,517,298 | 5/1985 | Tedder | 435/160 |
| 4,520,104 | 5/1985 | Heady et al. | 435/160 |
| 4,695,411 | 9/1987 | Stern et al. | 260/410.9 R |
| 5,190,868 | 3/1993 | Kokusho et al. | 435/134 |
| 5,354,878 | 10/1994 | Connemann et al. | 554/167 |
| 5,424,466 | 6/1995 | Stern et al. | 554/174 |

OTHER PUBLICATIONS

"Oil Crops of The World", edited by Robbelin et al., McGraw–Hill, Inc., 1989, pp. 226–243.

*Primary Examiner*—Herbert J. Lilling
*Attorney, Agent, or Firm*—Wayne C. Jaeschke; John E. Drach; Steven J. Trzaska

[57] ABSTRACT

The invention is an integrated process for making fatty acid lower alkyl ester from oilseeds or other natural oil-containing plant materials. The process comprises removing oil from the oilseeds and recovering it, to produce a reside comprising complex polymeric carbohydrates; saccharifying the deoiled oilseeds comprising complex polymeric carbohydrates to form saccharides; fermenting the saccharides to form ethanol or other lower alkyl alcohols; recovering the alcohol; and then transesterifying the recovered oil with the recovered alcohol to thereby produce glycerine and fatty acid lower alkyl esters.

14 Claims, 1 Drawing Sheet

5,710,030

PROCESS FOR PREPARING FUELS, FUEL SUBSTITUTES, AND FUEL SUPPLEMENTS FROM RENEWABLE RESOURCES

BACKGROUND OF THE INVENTION

1. Field of the Invention

Ethanol and other lower alkanols ($C_1$–$C_4$), produced by the fermentation of carbohydrates, have been used as fuel and also as a fuel supplement especially in blending with gasoline, or as a fuel substitute. On considering the energy required to produce lower alkanols by fermentation, only a slight increase in energy value is obtained using the alkanols as fuel.

Fatty acid methyl esters have also been prepared from methanol and renewable vegetable fats or oils. The methanol component, however, is usually derived from petrochemical processes.

This invention concerns an integrated process for the preparation of fatty acid lower-alkyl esters from renewable resources for use as fuel. The object of this invention is to recover as much heat content as available from vegetable matter, in particular from the seed, and convert it to a useable fuel. This process is superior to other processes in which the renewable resource is used to produce alcohol for fuel use, because it gives a higher yield of energy from the renewable resource in the final ester fuel product.

2. Description of the Related Art

Chemurgy is a branch of chemistry devoted to industrial utilization of organic raw materials particularly from farm products. This branch of chemistry is devoted to the use of renewable resources to form materials and energy.

The 1920's and 1930's was a period when there were large surpluses of agricultural materials and severe economic problems in farm areas. The idea of using farm commodities as chemical or industrial raw materials was seen as a great contribution to solving these economic problems. The area that seems to have been a common thread through the history of chemurgy is that of generating energy from biomass in some form as, for example, ethanol, the oldest man-made chemical made by fermentation.

The instant invention relates primarily to oilseeds and to an efficient method to produce fuel from oilseeds. The instant invention relates to (1) recovering the oil from an oil-bearing vegetable source such as oilseeds; (2) saccharifying the complex polymeric carbohydrate portions of deoiled seeds to simple fermentable sugars; (3) fermenting the saccharified sugars to produce alcohols; (4) recovering the alcohol produced by fermentation of the sugars; and (5) transesterifying the oil by reaction with the recovered alcohol.

It is known in the art to saccharify carbohydrates. For instance, U.S. Pat. No. 2,342,330 describes the treatment of starchy materials with an enzyme (diastase) to thereby break up the starch in the starchy material into sugars. Other patents that disclose useful saccharification processes include U.S. Pat. No. 4,361,551, U.S. Pat. No. 4,409,329 and U.S. Pat. No. 4,415,659, all of which patents are incorporated here by reference.

The fermentation of sugars to produce alcohol has been known for literally thousands of years. However, new methods of fermentation are constantly being developed. For instance, methods of producing alcohol (usually ethyl alcohol) by the fermentation of sugar-containing mixtures are disclosed in U.S. Pat. Nos. 4,425,433, 4,517,298 and 4,520,104. U.S. Pat. No. 4,520,104 is of special interest because it describes an improved process for the production of butanol by the fermentation of carbohydrates (i.e., sugars).

It has been known in the art to make transesterified ester by reacting the oil with an alcohol. Transesterified ester is formed by reacting a natural oil comprising animal fat or vegetable oils with an alcohol. These natural oils are triglycerides. Useful vegetable oils are sunflower oil, cottonseed oil, safflower oil, corn oil, soybean oil, rapeseed oil, meadowfoam oil and the like.

Alcohols utilized in forming transesterified esters are of the formula ROH wherein R is an aliphatic group that contains from 1 to about 24 carbon atoms. The R may be straight chained or branched chain, saturated or unsaturated. An illustrative but non exhaustive list of alcohols are: methyl alcohol, ethyl alcohol, n-propyl alcohol, isopropyl alcohol and the isomeric butyl alcohol. Preferably the alcohol is ethyl alcohol.

The transesterification occurs by mixing at least 3 moles of ROH per 1 mole of triglyceride. A catalyst, when employed, comprises alkali or alkaline earth metal alkoxides containing from 1 up to 6 carbon atoms. Preferred catalysts are sodium or potassium methoxide, calcium or magnesium methoxide, the ethoxides of sodium, potassium, calcium or magnesium and the isomeric propoxides of sodium, potassium, calcium or magnesium. The most preferred catalyst is sodium methoxide. The transesterification occurs at a temperature of from ambient up to the decomposition temperature of any reactant or product. Usually the upper temperature limit is not more than 150° C. and preferably not more than 120° C. Transesterification is an equilibrium reaction. To shift the equilibrium to the right it is necessary to use either a large excess of alcohol, or else remove glycerol as it is formed. When using an excess of alcohol, once the transesterification reaction is complete the excess alcohol is removed by distillation.

Processes for the transesterification of oils (i.e., triglycerides of higher fatty acids) to lower alkyl esters are described in U.S. Pat. Nos. 4,695,411 and 5,354,878. U.S. Pat. No. 5,354,878 describes a method of transesterifying vegetable oils such as corn oil, sunflower seed oil and the like, with a suitable monovalent alcohol such as methanol, isopropanol, butanol or multivalent alcohols such as trimethylolpropane but especially methanol.

Likewise, it has been known in the art to recover oil from oilseeds, particularly by expressing the oil from the seed by crushing. A particularly good description of known processes that can be used to recover the oil from oilseed is found in Oil Crops Of The World, edited by Robbelen et al. and published by McGraw-Hill Publishing Company in 1989, pages 226–243. These text pages are also incorporated by reference.

In spite of this prior art, it has never been known, been taught, or been recognized, to carry out the invention, which invention is an integral process for making lower alkyl esters from oilseeds.

Oilseeds differ from cereals in storing most of their energy reserves in the form of fats rather than starch. During the early formation of the seeds, sugars and starch are present but later, fats and protein start accumulating and residual starches may be present in only trace amounts. Oilseeds are grown for their oil not their protein content.

Suitable oilseeds include soybean seeds, groundnuts (peanuts), sesame seeds, safflower seeds, Brassica seeds (rapeseed, turnip seed, brown mustard, white mustard), sunflower seeds, cottonseed, linseed, palm kernels, and coconut meal.

Maize, an oilseed, usually called "corn" in the USA, has been a companion of man for at least 8,000 years. Maize, in the past, had not generally been considered to be an oil crop, primarily because it is usually relatively low in oil and secondly because its oil content was hidden. However, in recent years, high oil hybrids have been developed.

Traditional processing systems for oilseeds include a first step which is to "crush" the oilseeds or to separate cooked flakes of the oilseed by extraction so as to divide the oilseed into a crude oil component and a meal component. Mechanical pressing (the expeller process) is usually used if seed has 20% or more oil content. Otherwise, solvent extraction is used and sometimes a combination of the two processes. The recovered oil content is called a vegetable oil, if the oil remains liquid at room temperature. The recovered oil is called a vegetable fat, if it is semi-solid at room temperature.

BRIEF DESCRIPTION OF THE DRAWING

The single FIGURE of drawing shows a schematic representation of the integrated process, in the form of a block diagram flow sheet.

SUMMARY OF THE INVENTION

Figure 1:
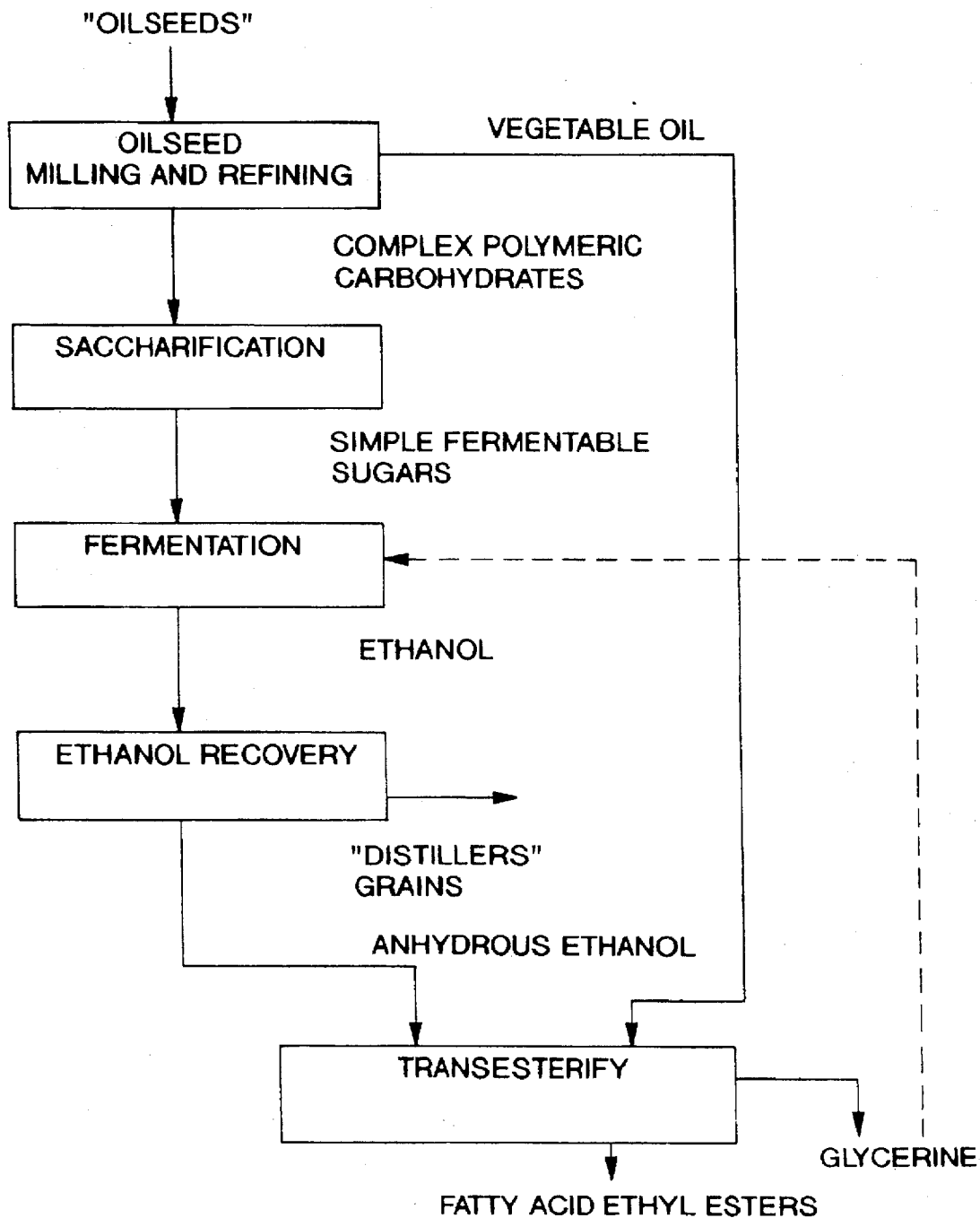

The integrated process of the invention is shown schematically in FIG. 1. Oilseeds are milled using essentially any customary milling procedures, for example corn wet milling, to produce a vegetable oil and a residual mixture of complex polymeric carbohydrates comprised of celluloses, starches, and others. The complex polymeric carbohydrates are depolymerized (saccharified) by chemical (i.e., strong acids) or biochemical (i.e., using enzymes) means to produce a high yield of fermentable sugars, or by a combination of acid and enzyme steps. These sugar-containing mixtures are fermented using yeast, bacteria, or fungi, to thereby convert the sugars to lower alkanols, especially ethanol. If azeotropic distillation is used, nearly anhydrous alkanols can be recovered. Also recovered is the grain residue which may be used in animal feed.

Next, the glycerides in the oil that had been obtained from the oilseed and the alcohol, are transesterified to produce fatty acid alkyl esters, preferably lower alkyl esters, which can be used as a fuel, fuel substitute, or fuel supplement. A coproduct of the transesterification is glycerine. While the coproduct glycerine has valuable established applications, it also represents additional energy value to be recovered as useable fuel. Fermentation of the coproduct glycerine to additional lower alcohol (e.g., ethanol) may be used to recover this energy value for incorporation in the fuel.

In addition, the anhydrous glycerine resulting from transesterification may be used to obtain additional process energy economy in the integrated process since it can provide a driving force as part of the necessary alcohol/water separation. For example, distillation of ethanol-water from fermentation both yields an azeotropic mixture of ethanol and water. Contacting these azeotropic vapors with a semipermeable membrane using anhydrous glycerine on the opposite side of the membrane could reduce energy expended in breaking the azeotrope. The now wet glycerine is then used in a subsequent fermentation. Thus, glycerine not only contributes to the energy value that is recovered from oilseeds as useable fuel by the production of additional lower alcohol but also the glycerine contributes to energy economy since it can provide a driving force in alcohol/water separation.

In some cases, it may be desirable to sell a portion of the vegetable oil in the commercial market, substituting other fats or oils in the transesterification operation; other fats or oils can be substituted for either economic reasons or to impart desirable physical or chemical properties to the fuel product.

DESCRIPTION OF THE PREFERRED EMBODIMENTS

The invention is an integrated process for making fatty acid alkyl esters from oil-containing plant material wherein oil is extracted from the plant material. After the oil has been removed, the residue plant material is subjected to saccharification of the complex polymeric carbohydrates of the plant material to form a mixture that includes fermentable sugars. This mix then is fermented to produce alcohol. Preferably, the alcohol is ethanol, but any alcohol can be useful, although lower alkanols, i.e., $C_1$–$C_4$, are preferred. To complete the integrated process, the lower alkyl alcohol and the oil are subjected to transesterification to produce lower alkyl esters which are particularly useful as fuel.

In another embodiment, the invention is an integrated process for making fatty acid ester from oilseeds. The system in the integrated process comprises (a) milling and refining oilseeds to extract oil to form a first fraction which is oil and a second fraction which is the residual product remaining after oil is recovered; (b) saccharifying the carbohydrates in the second residual fraction to form a solution comprising fermentable sugars; (c) fermenting the solution to form lower alkyl alcohol; (d) recovering the lower alkyl alcohol and finally reacting the alcohol with the extracted oil so as to produce glycerine and fatty acid lower alkyl esters.

In another embodiment, the invention is an integrated process for making ethyl ester of linoleic acid from corn (i.e., maize). The oil that is derived from corn (i.e., corn oil) is based on a mixture of fatty acids but primarily the oil is based on linoleic oil (i.e., a triglyceride of linoleic acid). In this embodiment of the invention, corn oil is extracted from corn. The deoiled corn which remains after the oil is removed is saccharified to form sugars; the sugars are fermented to form ethanol; the ethanol is recovered by azeotropic distillation, and as a final step, the corn oil is transesterified by reaction with the ethanol to thereby form primarily the ethyl ester of linoleic acid.

The invention envisions that the integrated process would be particularly suitable to be carried out in rural areas of this country as well as in less developed countries with a minimum of investment. Further, it was envisioned that the process could be used to process oilseeds other than corn. It was envisioned that once an investment was made in suitable machinery, the oilseed could be processed fairly easily to make ethyl ester fuels. The ingredients that are needed to carry out the invention other than the oilseed would be few in number. Other ingredients that could be needed would include yeasts, acid, enzymes and the like.

It is further contemplated that any oil-containing vegetable matter, not just corn or other oilseeds could be used according to the invention to make fatty acid lower alkyl esters.

The integrated process of the invention is shown in diagram form in FIG. 1 and is believed to be self-explanatory in the light of discussions already set forth above.

What is claimed is:

1. An integrated process for manufacturing a composition of fatty acid esters, useful as or in a fuel, from oil-containing natural plant material, comprising (a) removing the oil from said oil-containing plant material, and recovering it, to produce a residue comprising complex polymeric carbohydrates;

(b) saccharifying deoiled plant material comprising complex polymeric carbohydrate to form saccharides;

(c) fermenting the saccharides to form alkanol; and (d) reacting said recovered alkanol with the oil extracted according to step (a) to effect transesterification and to produce fatty acid lower alkyl esters useful as a fuel or fuel additive.

2. The process of claim 1, wherein said plant material comprises cottonseed.

3. The process of claim 1, wherein said plant material comprises corn.

4. The process of claim 1, wherein said plant material comprises soybeans.

5. The process of claim 1, wherein said alkanol comprises a lower, $C_1$–$C_4$ alkanol.

6. The process of claim 5, wherein said alkanol comprises ethanol.

7. The process of claim 1, wherein said transesterified esters comprise fatty acid esters of ethanol.

8. An integrated process for the production of lower alkyl fatty acid esters from oilseeds comprising the step of (a) milling and refining oilseeds to thereby extract oil from said oilseeds to thereby form two fractions, wherein the first of said two fractions is the extracted oil and the second of said two fractions is the product remaining after removal of the first fraction, said second fraction comprising complex polymeric carbohydrates;

(b) saccharifying the carbohydrates in the second of said two fractions to form a solution comprising fermentable sugars;

(c) fermenting the product of step (b) to form lower alkyl alcohol, and recovering the lower alkyl alcohol product; and (d) reacting the lower alkyl alcohol product of step (c) with the extract oil product of step (a) to transesterify said extract oil and thereby produce glycerine and fatty acid lower alkyl esters.

9. The integrated process of claim 8, wherein the oilseeds are selected from the group consisting of soybean seeds, groundnuts, sesame seeds, safflower seeds, Brassica seeds, sunflower seeds, cottonseed, linseed, palm kernels, coconut meal, and mixtures thereof.

10. The integrated process of claim 9, wherein said lower alkyl alcohol is ethyl alcohol and wherein said saccharifying is carried out by a method selected from the group consisting of an acid saccharification method; an acid-enzyme saccharification method; and an enzyme saccharification method.

11. The integrated process of claim 9, wherein said lower alkyl alcohol is recovered from the product of step (c) by distillation.

12. The integrated process of claim 8, wherein lower alkyl alcohol is recovered from the product of step (c) by the addition of a suitable hydrocarbon solvent thereby forming an alcohol-organic solvent extract phase, and separating said alcohol from said alcohol-organic solvent phase to recover said alcohol.

13. An integrated process for manufacturing an ester comprising ethyl esters of linoleic acid from corn comprising (a) extracting oil from said corn;

(b) saccharifying the deoiled corn from step (a) to thereby form a mixture containing sugars;

(c) fermenting the product of step (b) using yeast, bacteria or fungi to convert said sugars to ethanol;

(d) recovering substantially anhydrous ethanol by azeotropic distillation; and (e) transesterifying said oil extracted from said corn according to step (a) by reacting said oil with said substantially anhydrous ethanol product of step (d).

14. The integrated process of claim 13, wherein said lower alkyl alcohol is selected from the group consisting of methyl alcohol, ethyl alcohol, propyl alcohol, butyl alcohol and mixtures thereof.

* * * * *